(12) United States Patent
Evans et al.

(10) Patent No.: US 8,546,592 B2
(45) Date of Patent: Oct. 1, 2013

(54) OLEFIN EPOXIDATION PROCESS

(75) Inventors: Wayne Errol Evans, Richmond, TX (US); Paul Michael McAllister, Houston, TX (US); Randall Clayton Yeates, Sugar Land, TX (US); Jeffrey Michael Kobe, Houston, TX (US)

(73) Assignee: Shell Oil Company, Houston, TX (US)

( * ) Notice: Subject to any disclaimer, the term of this patent is extended or adjusted under 35 U.S.C. 154(b) by 58 days.

(21) Appl. No.: 13/246,325

(22) Filed: Sep. 27, 2011

(65) Prior Publication Data

US 2012/0077997 A1    Mar. 29, 2012

Related U.S. Application Data (60) Provisional application No. 61/387,858, filed on Sep. 29, 2010.

(51) Int. Cl.
  *C07D 301/03*    (2006.01)
  *C07C 29/00*    (2006.01)

(52) U.S. Cl.
  USPC ............................ 549/536; 549/534; 568/867

(58) Field of Classification Search
  USPC .................... 549/536, 534; 568/867
  See application file for complete search history.

(56) References Cited

U.S. PATENT DOCUMENTS

| | | | |
|---|---|---|---|
| 4,761,394 A | 8/1988 | Lauritzen | 549/536 |
| 4,766,105 A | 8/1988 | Lauritzen | 502/216 |
| 4,845,296 A | 7/1989 | Ahmed et al. | 564/477 |
| 4,874,879 A | 10/1989 | Lauritzen et al. | 549/536 |
| 5,155,242 A | 10/1992 | Shankar et al. | 549/534 |
| 5,801,259 A | 9/1998 | Kowaleski | 549/536 |
| 6,080,897 A | 6/2000 | Kawabe | 568/858 |
| 6,717,001 B2 | 4/2004 | Evans et al. | 549/536 |
| 7,102,022 B2 | 9/2006 | Evans et al. | 549/536 |
| 7,193,094 B2 | 3/2007 | Chipman et al. | 549/536 |
| 7,237,677 B2 | 7/2007 | Berg | 206/581 |
| 7,348,444 B2 | 3/2008 | Evans et al. | 549/534 |
| 7,485,597 B2 | 2/2009 | Lockemeyer et al. | 502/216 |
| 7,657,331 B2 | 2/2010 | Chipman et al. | 700/28 |
| 2007/0129557 A1 | 6/2007 | Chipman et al. | 549/535 |
| 2009/0069583 A1 | 3/2009 | Rizkalla et al. | 549/536 |
| 2009/0234144 A1 | 9/2009 | Bos et al. | 549/534 |
| 2009/0281339 A1 | 11/2009 | Matusz et al. | 549/523 |

FOREIGN PATENT DOCUMENTS

| | | |
|---|---|---|
| EP | 1458698 | 11/2002 |
| EP | 2155708 | 5/2008 |
| GB | 1122731 | 8/1968 |
| WO | WO2004007873 | 1/2004 |
| WO | WO2004007874 | 1/2004 |
| WO | WO2006028544 | 3/2006 |
| WO | WO2006102189 | 9/2006 |

OTHER PUBLICATIONS

Kirk-Othmer's Encyclopedia of Chemical Technology, 3rd ed., vol. 9 (1980), p. 445-447.
Encyclopedia of Catalysts, vol. 3 (2003) p. 246-264.
Brunauer, Emmet and Teller in J. Am. Chem. Soc. 60 (1938), p. 309-316.
Kaoru Fujimoto et al., "Olefin Oxidation-Palladium Salt-Active Charcoal Catalysis," Industrial Engineering Chemistry Product Research and Development, vol. 11, No. 3, 1972, pp. 303-308.

*Primary Examiner* — Taylor Victor Oh (57) ABSTRACT

A process for the production of an olefin oxide, which process comprises reacting a feed comprising an olefin and oxygen in a reactor tube in the presence of a silver-containing catalyst, wherein the presence of water in the catalyst bed is controlled such that the ratio of the partial pressure of water ($PPH_2O$) divided by the vapor pressure of water ($VPH_2O$) is less than 0.006, preferably less than 0.004.

24 Claims, 3 Drawing Sheets

OLEFIN EPOXIDATION PROCESS

This application claims the benefit of U.S. Provisional Application 61/387,858 filed Sep. 29, 2010.

FIELD OF THE INVENTION

The present invention relates to a process for the production of an olefin oxide, a 1,2-diol, a 1,2-diol ether, 1,2-carbonate or an alkanolamine.

BACKGROUND OF THE INVENTION

In olefin epoxidation an olefin is reacted with oxygen to form an olefin epoxide, using a catalyst comprising a silver component, usually with one or more further elements deposited therewith on a support. The olefin oxide may be reacted with water, an alcohol, carbon dioxide or an amine to form a 1,2-diol, a 1,2-diol ether, 1,2-carbonate or an alkanolamine. Thus, 1,2-diols, 1,2-diol ethers, 1,2-carbonates and alkanolamines may be produced in a multi-step process comprising olefin epoxidation and converting the formed olefin oxide with water, an alcohol, carbon dioxide or an amine.

The performance of the epoxidation process may be assessed on the basis of the selectivity, the catalyst's activity and stability of operation. The selectivity is the molar fraction of the converted olefin yielding the desired olefin oxide. The catalyst is subject to an ageing-related performance decline during normal operation. The ageing manifests itself by a reduction in the activity of the catalyst. Usually, when a reduction in activity of the catalyst is shown, the reaction temperature is increased in order to compensate for the reduction in activity, however at the expense of selectivity. In the typical operation of a fresh catalyst, the process is operated at a reaction temperature of up to about 250° C. Upon catalyst ageing the reaction temperature may gradually be increased to values substantially above 250° C. until the reaction temperature becomes undesirably high or the selectivity becomes undesirably low, at which point in time the catalyst is deemed to be at the end of its lifetime and would need to be exchanged. It goes without saying that from an economical point of view it is highly desirable to improve the performance of the catalyst and to extend its lifetime as much as possible. Quite modest improvements in the maintenance of selectivity over long periods yield huge dividends in terms of efficiency in the olefin epoxidation process and, if applicable, also in the overall process for the production of a 1,2-diol, a 1,2-diol ether, 1,2-carbonate or an alkanolamine.

Therefore, for decades much research has been devoted to improving the activity, the selectivity and the lifetime of the catalysts, and to find process conditions which enable full exploitation of the catalyst performance. For example, it is well known that low $CO_2$ levels are useful in improving the selectivity of high selectivity catalysts. See, e.g., U.S. Pat. No. 7,237,677; U.S. Pat. No. 7,193,094; US 2007/0129557; WO 2004/07873; WO 2004/07874; and EP 2,155,708. These patents also disclose that water concentration in the reactor feed should be maintained at a level of at most 0.35 mole percent, preferably less than 0.2 mole percent. Other patents disclose control of the chloride moderator to maintain good activity. See, e.g., U.S. Pat. No. 7,657,331; EP 1,458,698; and US Pub. Pat. App. 2009/0069583. Still further, there are many other patents dealing with the epoxidation process and means to improve the performance of the catalyst in the process. See, e.g., U.S. Pat. Nos. 7,485,597, 7,102,022, 6,717,001, 7,348,444, and US Pub. Pat. App. 2009/0234144.

Notwithstanding the improvements already achieved, there is a desire to further improve the performance of the silver-containing catalysts in the production of an olefin oxide, a 1,2-diol, a 1,2-diol ether, a 1,2-carbonate or an alkanolamine.

SUMMARY OF THE INVENTION

The present invention provides a process for the production of an olefin oxide, which process comprises reacting a feed comprising an olefin and oxygen in the presence of a supported silver-containing catalyst loaded into a reactor tube (i.e., the catalyst bed), wherein the presence of water at any point in the catalyst bed is controlled such that the ratio of the partial pressure of water ($PPH_2O$) divided by the vapor pressure of water ($VPH_2O$) is less than 0.006, preferably less than 0.004. As shown in the examples which follow, even the low levels of water that had been considered acceptable in the past are detrimental to the performance of a silver-containing catalyst.

This invention constitutes a means to reduce the rate of selectivity loss by an epoxidation catalyst while in operation that is different from the well-known effects of time and temperature described above in the prior art. In this invention the water vapor concentration in the catalyst bed is reduced to certain levels in order to reduce significantly the rate of selectivity loss and the overall selectivity loss during the catalyst operational cycle. This is different from the prior art view, because the primary effect of reducing water vapor concentration is not a slower decline rate due to lower operating temperature for the catalyst. In this invention, we have found that water causes another ageing mechanism which may actually lower the rate of temperature increase but at the same time cause accelerated selectivity loss. In this invention we have found that significantly lower concentrations of water in the vapor phase at conditions where condensation of liquid water is not possible has resulted in changes in the catalyst that lead to loss of selectivity. The hygroscopic nature of the catalyst or catalyst support results in adsorption of water on the surface of the catalytic material even when conditions are such that liquid water should not be present on the catalyst or internal reactor surfaces. i.e., well above the dew point of water. Thus, the presence of excess water in the vapor phase will suppress selectivity and lead to increased rates of sintering or losses of key water soluble dopants from the catalyst surface.

In the present invention, we have found that the redistribution of key water soluble dopants on the surface of the catalyst can be greatly reduced and therefore the catalyst selectivity loss rates can be reduced significantly by reduction of the ratio of the partial pressure of water ($PPH_2O$) divided by the vapor pressure of water ($VPH_2O$) at the inlet and throughout the catalyst bed. Vapor phase water is introduced in a typical commercial reactor in the feed gas at the inlet of the reactor as well as by generation within the reactor due to the complete combustion of a portion of the ethylene fed to the reactor to $CO_2$ and water. See, e.g., US Pub. Pat. App. 2009/0234144, which disclosure is incorporated in its entirety herein. There are a number of ways by which the ratio of the partial pressure of water ($PPH_2O$) divided by the vapor pressure of water ($VPH_2O$) can be reduced. These include:

Increased cooling of the overhead streams coming from the ethylene oxide ("EO") removal and/or $CO_2$ removal sections of the plant that return to the reactor.

Diversion of less of the recycle gas through the $CO_2$ absorber.

Operation of the EO and $CO_2$ absorbers at lower temperature.

Increasing the Gas Hourly Space Velocity at fixed EO production to reduce the water concentration gradient increase in the reactor.

Reduction in work rate or EO production per unit volume of catalyst to reduce the amount of $H_2O$ formed in the reactor.

Utilization of catalysts with higher selectivity such that the amount of water produced across the catalyst bed is reduced for a given EO production rate.

Reducing the reactor operating pressure so as to reduce the partial pressure of $H_2O$.

Operation of the reactor at higher temperature than required to increase the vapor pressure of water.

These are some of the means by which the ratio of the partial pressure of water ($PPH_2O$) divided by the vapor pressure of water ($VPH_2O$) in the reactor/catalyst bed can be reduced, but this is not an exhaustive list. The concept can be applied to existing plants by making changes in operating variables and/or changes to plant hardware such as heat exchangers, absorbers, and compressors. The concept can be applied to new plants in the design phase as well.

A quantitative analysis method has been developed to determine the level of water vapor which causes accelerated selectivity loss of epoxidation catalysts while in operation. Extensive evaluation of post mortem results of spent catalysts demonstrated that surface concentrations of water soluble dopants as measured by X-ray Photoelectron Spectroscopy ("XPS") were reduced significantly when the ratio of the water partial pressure in the gas phase to the vapor pressure ($PPH_2O/VPH_2O$) of water at the location of the sample in the reactor during operation exceeded 0.004. The reduction of surface concentration of these water soluble dopants is directly linked to selectivity loss of the catalyst. Samples which were not exposed to $PPH_2O/VPH_2O>0.004$ showed much less reduction in the surface concentration of water soluble dopants and much less selectivity loss. It is most preferable that the ratio of $PPH_2O/VPH_2O$ is less than 0.004 over the entire length of the catalyst bed. But advantages are also shown where the ratio is less than 0.004 over a portion of the catalyst bed—for example where the ratio is less than 0.004 over greater than 50% of the reactor tube length (defined as the length from the catalyst bed inlet to the catalyst bed outlet), preferably over greater than 80% of the reactor bed length.

While ratios of $PPH_2O/VPH_2O<0.004$ are highly desirable, it may not be possible to achieve this in many commercial plants throughout the entire catalyst bed due to hardware limitations, operating constraints, or EO production requirements. This does not preclude a plant from taking advantage of the concept. Reduction of $PPH_2O/VPH_2O$ is expected to be beneficial no matter what the starting point. Thus, if a plant can reduce $PPH_2O/VPH_2O$ from 0.007 to 0.006 one would still expect a beneficial effect. Likewise, it may be possible to increase the portion of the catalyst bed that operates at $PPH_2O/VPH_2O<0.004$. This will have a beneficial effect as it will reduce the rate of selectivity loss from this portion of the bed and will have a beneficial effect on the rest of the catalyst bed which may operate above this threshold.

The finding that water vapor concentrations can cause accelerated selectivity loss is an unexpected result as the traditional view has been that higher temperatures were the primary driving force behind selectivity loss. Thus, the invention described here is fundamentally different from prior methods attempted to increase initial selectivity and to reduce the rate of selectivity decline for a given catalyst. Another unexpected aspect of the invention is that the moderator level needs to be shifted, usually towards higher levels, as the water level is decreased, in order to maintain optimum performance. This is not intuitive—water level has little overall impact on catalyst activity, and the "Q" factor optimum is primarily a function of temperature, so most operators wouldn't see any reason to change the "Q" factor with water levels. Those that do would change the "Q" factor proportionally to the water level, in order to compensate for $H_2O$ adsorption, but in most situations, this change is in the wrong direction. The "Q" factor is taught in U.S. Pat. No. 7,193,094, which patent is incorporated by reference herein. However, in the '094 patent, the moderator level is primarily a function of the reactor temperature. This current invention reveals that proper control of the "Q" factor requires re-optimization of the moderator level whenever any significant shift in water levels occurs in the catalyst bed.

The invention also provides a method of using an olefin oxide for making a 1,2-diol, a 1,2-diol ether, 1,2-carbonate or an alkanolamine comprising converting the olefin oxide into the 1,2-diol, the 1,2-diol ether, 1,2-carbonate or the alkanolamine, wherein the olefin oxide has been obtained by the process according to this invention.

DETAILED DESCRIPTION OF THE INVENTION

I. Method to Calculate $PPH_2O/VPH_2O$

The following steps provide a full description of the methodology required to calculate the partial pressure of water in the gas phase at multiple positions within the catalyst bed of a reactor tube and the vapor pressure of water at each axial position as well. Finally, the ratio of water partial pressure to water vapor pressure is calculated so that it can be determined if the water concentration in the gas phase at each axial position will cause increased selectivity loss.

Step A. Measure or Estimate the Axial Gas Temperature Profile in the Catalyst Bed.

The axial gas temperature profile within a tube packed with catalyst can be measured directly with thermocouples placed in selected tubes in the reactor. In many cases, 5-20 tubes in the reactor will have an internal catalyst bed thermocouple sheath installed along the length of the reactor. Each thermocouple sheath typically has 5-10 temperature indicating points at known positions along its length. These thermocouples placed in a select number of tubes provide a close approximation of the gas temperature in the remaining tubes in the reactor.

In case the reactor does not have thermocouples placed in the catalyst bed to measure the axial gas temperature profile, the gas temperature can be estimated from the outlet gas temperature ("OGT"), and coolant temperature measurements. For example in one case, the measured OGT was 242.9° C. and the following coolant temperature measurements were available even though a thermocouple was not placed in the catalyst bed.

| 1.33 m Coolant | 2.33 m Coolant | 3.57 m Coolant | 4.57 m Coolant | 5.73 m Coolant | 6.73 m Coolant | 7.07 m Coolant | 9.07 m Coolant | 10.33 m Coolant | 11.33 m Coolant |
|---|---|---|---|---|---|---|---|---|---|
| 235.0 | 235.2 | 235.4 | 235.5 | 235.6 | 235.7 | 235.9 | 236.0 | 236.3 | 236.4 |

Typically at a distance of 1 meter into the catalyst bed, the gas temperature will be equal to the coolant temperature. At subsequent distances into the reactor, the gas temperature in the catalyst bed will exceed the coolant temperature by ~1-15° C. in reactors using water as a coolant and by 5-30° C. in reactors using a hydrocarbon coolant. Even higher differences between the gas temperature and the coolant can occur in situations where subcooled coolant is supplied to the reactor or the reactor is being operated at severe conditions. To approximate the gas temperature in the catalyst bed of a water cooled reactor, a constant offset can be added to the coolant temperatures beyond the 1 meter distance. The difference between the coolant temperature at the outlet of the reactor and the OGT provides a close approximation provided the OGT is measured before significant cooling of the reactor product gas occurs.

Offset=OGT−11.33 m Coolant Temperature

Offset=242.9° C.−236.4° C.=6.5° C.

Thus, the gas temperatures in the catalyst bed would be:

1.33 m Catalyst=235.0° C.+6.5° C.=241.5° C.
2.33 m Catalyst=235.2° C.+6.5° C.=241.7° C.
3.57 m Catalyst=235.4° C.+6.5° C.=241.9° C.
11.33 m Catalyst=236.4° C.+6.5° C.=242.9° C.

In the case of a boiling hydrocarbon cooled reactor, there is often a larger difference between outlet gas and coolant temperatures at the outlet of the reactor and the difference between coolant temperature and gas temperature in the catalyst bed may increase as the distance from the inlet of the catalyst bed increases. As an example, if: OGT=250° C. for a hydrocarbon cooled reactor and coolant temperature near the outlet of the reactor was 238° C., then the following maximum offset would be found at the reactor outlet:

Maximum Offset−OGT−temperature at 11.33 meter for coolant=250° C.−238.0° C.=12° C.

In most cases a good approximation to the axial gas temperature profile through the catalyst bed can be obtained by assuming a linearly increasing catalyst temperature from near the inlet of the catalyst bed to the outlet of the bed. The gas temperature profile can be estimated by the following equation:

Gas Temperature($z$)=Coolant Temperature($z$)+(Maximum Offset)times(($z-z_{heatup}$)/($L-z_{heatup}$)) where:

Gas Temperature($z$) is the temperature of the gas within the catalyst bed at the axial distance, z as measured from the inlet of the bed.
Coolant Temperature($z$) is the coolant temperature at position z.
Maximum Offset is described above.
$z_{heatup}$ is the length of the tube required to bring the inlet gas up to the coolant temperature. Typical is approximately 1 meter.
L is the total length of the catalyst bed.

Other methods may be used to measure or estimate the gas temperature in the catalyst bed depending on the reactor configuration, mode of operation, and available measurements of actual conditions.

Step B. Measure or Estimate the Axial Pressure Profile within the Catalyst Bed
  a. The pressure of the gas in the catalyst bed must be measured or estimated at each point for which it is desired to calculate the partial pressure of the $H_2O$ vapor in the catalyst bed.
  b. Normally, the gas pressure is measured at the inlet and outlet of the catalyst bed by pressure-indicating transducers, gauges or other devices.
  c. The gas pressure throughout the catalyst bed can be closely approximated by assuming the pressure changes linearly with position in the catalyst bed from the inlet value to the outlet value.
  d. The following equation can be applied to estimate the pressure at each axial position if the inlet and outlet pressure values are known.

Pressure($z$)=Inlet Pressure+(Outlet Pressure−Inlet Pressure)times($z/L$)

Where:
  1. Pressure(z) is the pressure at position z within the catalyst bed.
  2. Inlet Pressure is the absolute pressure as measured at the inlet of the reactor.
  3. Outlet Pressure is the absolute pressure as measured at the outlet of the reactor.
  4. Z is the distance from the inlet of the catalyst bed.
  5. L is the overall length of the catalyst bed.

Other methods or models may be applied to calculate the axial pressure profile in the reactor if outlet pressure measurements are not available.

Step C. Calculate the Axial Water Partial Pressure Profile within the Catalyst Bed.
  a. Given the water concentrations in the gas phase entering and exiting the reactor along with the axial pressure profile determined in Step B, the axial profile of the water partial pressure can be calculated by the following equation.
  b. In the following calculation, it is assumed that the mole fraction of $H_2O$ increases linearly from the inlet to the outlet of the catalyst bed. Experimental data have shown this to be a reasonable assumption.

$PPH_2O(z)$=([$H_2Oin$]+([$H_2Oout$]−[$H_2Oin$])times($z/L$)) times Pressure($z$) where:

$PPH_2O(z)$ is the partial pressure of water in the gas phase a distance z from the inlet of the catalyst bed.
[$H_2Oin$] is the mole fraction of water in the gas phase at the entrance to the catalyst bed. [$H_2Oin$] can be measured by a number of analytical methods, including the well-known Karl Fischer Titration method (ASTM E203-08) or calculated based on process knowledge and measurements of temperature, pressure, and flow in the process.
[$H_2Oout$] is the mole fraction of water in the gas leaving the catalyst bed and can be measured by a number of analytical techniques, including ASTM E203-08.

In the absence of actual measurements of [H$_2$Oout], the stoichiometry of the complete combustion of ethylene to CO$_2$ and H$_2$O can be used to calculate accurately the outlet water mole fraction provided the amount of CO$_2$ formed in the reactor has been measured and the inlet H$_2$O mole fraction is known. For each mole of CO$_2$ formed in the reactor, one mole of H$_2$O will be formed. In these instances, [H$_2$Oout] can be calculated accurately as follows:

[H$_2$Oout]=[H$_2$Oin]+([CO$_2$out]−[CO$_2$in]) where:

[CO$_2$out] is the mole fraction of CO$_2$ out of the reactor
[CO$_2$ in] is the mole fraction of CO$_2$ into the reactor
Step D. Calculate the Water Vapor Pressure Axial Profile
a. The vapor pressure of water can be calculated at each axial position within the catalyst bed using the following correlation.

VPH$_2$O(bara)=exp($A+B/T+C$ ln($T$)+$DT^E$)times10$^{-5}$
where

VPPH$_2$O is the vapor pressure of water in bara
A=73.649
B=−7258.2
C=−7.3037
D=0.0000041653
E=2
T is the gas temperature in ° K.
The results of an example calculation are shown below.

| Axial Position (z) | 1.33 | 2.33 | 3.57 | 4.57 | 5.73 | 6.73 | 7.07 | 9.07 | 10.33 | 11.33 | m |
|---|---|---|---|---|---|---|---|---|---|---|---|
| Gas Pressure in the Catalyst Bed | 19.1 | 18.9 | 18.6 | 18.4 | 18.2 | 17.9 | 17.9 | 17.4 | 17.2 | 16.9 | bara |
| Gas Temperature in Catalyst Bed | 236.6 | 238.0 | 239.7 | 241.0 | 242.5 | 243.8 | 244.3 | 246.9 | 248.6 | 250.0 | ° C. |
| Gas Temperature in Catalyst Bed | 509.8 | 511.1 | 512.8 | 514.1 | 515.6 | 516.9 | 517.5 | 520.1 | 521.8 | 523.2 | °K |
| Water Vapor Pressure | 31.5 | 32.3 | 33.2 | 34.0 | 34.9 | 35.7 | 36.0 | 37.7 | 38.8 | 39.7 | bara |

Reference: Gallagher, J. S., Haar, L., Kell, G. S. NBS/NRC Steam Tables. *Thermodynamic and Transport Properties and Computer Programs for Vapor and Liquid States of Water in SI Units*. Hemisphere Publish Corporation, Washington, 1984.

Step E. Calculate the Ratio of PPH$_2$O to VPH$_2$O
Calculation of the ratio of water partial pressure in the gas phase relative to the vapor pressure is a straightforward calculation from the results of Steps C and D.

Ratio=PPH$_2$O(z)/VPH$_2$O(z) where

PPH$_2$O(z) is the partial pressure of water at a distance z from the inlet of the catalyst bed.
VPH$_2$O(z) is the vapor pressure of water at a distance z from the inlet of the catalyst bed.
The results of an example calculation are shown below.

| Axial Position (z), m | 1.33 | 2.33 | 3.57 | 4.57 | 5.73 | 6.73 | 7.07 | 9.07 | 10.33 | 11.33 | m |
|---|---|---|---|---|---|---|---|---|---|---|---|
| Water Partial Pressure | 0.111 | 0.121 | 0.133 | 0.143 | 0.153 | 0.162 | 0.165 | 0.182 | 0.192 | 0.200 | bara |
| Water Vapor Pressure | 31.5 | 32.3 | 33.2 | 34.0 | 34.9 | 35.7 | 36.0 | 37.7 | 38.8 | 39.7 | bara |
| Ratio PPH2O/VPH2O | 0.00352 | 0.00375 | 0.00401 | 0.00419 | 0.00439 | 0.00454 | 0.00458 | 0.00483 | 0.00495 | 0.00503 | |

If the values in the table above exceed 0.004, then it would be expected that the catalyst will show accelerated decline resulting from the presence of water.

II. Process for Making Olefin Oxide

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Typically, the olefin is a mono olefin, for example 2-butene or isobutene. Preferably, the olefin is a mono-α-olefin, for example 1-butene or propylene. The most preferred olefin is ethylene.

The olefin content of the feed is typically between 15 and 50 mole percent, relative to the total feed. In preferred embodiments, amongst others, the olefin content of the feed is maintained at a value of at least 25 mole-%. Typically the olefin content of the feed is maintained at the value as defined for at least a period which is sufficient to effect an olefin oxide production of at least 1,000 kmole, more typically at least 5,000 kmole, most typically at least 10,000 kmole, of olefin oxide per m$^3$ catalyst bed, preferably up to the end of the catalyst's lifetime, that is when the catalyst will be exchanged and/or rejuvenated. As used herein, the feed is considered to be the composition which is contacted with the catalyst.

The direct oxidation of an olefin to the corresponding olefin oxide can be air-based or oxygen-based, see Kirk-Othmer's Encyclopedia of Chemical Technology, 3rd ed., Vol. 9 (1980) p. 445 to 447, and Encyclopedia of Catalysts, Vol. 3 (2003) p. 246-264. In the air-based processes air or air enriched with oxygen is fed directly to the system while in the oxygen-based processes high-purity (above 95 mol-%) oxygen is employed as the source of the oxidizing agent. Presently most ethylene oxide production plants are oxygen-based and this is the preferred embodiment of the present invention.

The oxygen content of the feed is within the broad range of from 3 to 20 mole-%, preferably from 5 to 12 mole-%, relative to the total feed.

In order to remain outside the flammability limit of the reaction mixture, the oxygen content of the feed is usually balanced with the olefin content. The actual safe operating ranges depend, along with the gas composition (reactants and balance gases), also on individual plant conditions such as temperature and pressure.

In addition to the olefin and oxygen, the feed may contain one or more optional components, such as carbon dioxide, a reaction modifier (moderator), a reaction co-modifier (co-moderator) and balance inert gases.

Carbon dioxide is a by-product of the olefin oxidation process. Since unconverted olefin is continuously recycled, and since carbon dioxide in the feed will have an adverse effect on catalyst activity, accumulation of carbon dioxide will be avoided by continuously removing carbon dioxide from the recycle gas. This may be done by venting and by continuous absorption of the formed carbon dioxide. Currently concentrations of carbon dioxide in the feed gas stream as low as 0.2-0.3 mole-% are practical, though amounts of as high as 3 mole-% are often found in practice.

Reaction modifiers and co-modifiers may be added to the feed for increasing the selectivity, suppressing the undesirable oxidation of olefin and of the olefin oxide to carbon dioxide and water. Many organic compounds, especially organic halides but also amines, ammonia, organometallic compounds and aromatic hydrocarbons are known to be effective in this respect. Organic halides are the preferred reaction modifiers and they are effective without suppressing the desired reaction when used in quantities ranging from 0.1 to 25 parts per million by volume (ppmv), in particular from 0.3 to 20 ppmv, relative to the total feed. Dependent of the silver-containing catalyst employed, the reaction modifier content of the feed may be optimized from time to time during operation if the maximum achievable selectivity is to be maintained. Preferred organic halides are $C_1$ to $C_8$ chloro hydrocarbons or bromo hydrocarbons. More preferably they are selected from the group of methyl chloride, ethyl chloride, ethylene dichloride, ethylene dibromide, vinyl chloride or a mixture thereof. Most preferred reaction modifiers are ethyl chloride and ethylene dichloride.

Typically, as the organic halide moderator level is increased, the catalyst activity decreases, and the catalyst selectivity passes through a maximum. Therefore, typical operation of an ethylene oxide plant involves maintaining the moderator level to maintain this optimum selectivity. As disclosed in U.S. Pat. No. 7,193,094, as the hydrocarbon composition changes, the moderator level has to change as well, in order to maintain operation at maximum selectivity. Likewise, as the catalyst temperature increases, the moderator level also needs to increase. This current invention teaches that as the water concentration in the catalyst bed changes, the moderator level needs to be re-optimized as well, regardless of whether or not the catalyst temperature or hydrocarbon composition has changed. It has been found that with fresh catalysts, increasing the water level led to almost no change in catalyst activity (i.e., operating temperature at a fixed EO production rate), but nonetheless the moderator level needed to be lowered significantly in order to maintain optimum operation. Practically, changes in chloride levels less than 0.2 ppm will have an impact on catalyst performance that cannot be measured precisely. It has been found that increasing the inlet water level by 1% typically required a reduction in the optimal moderator level between 0.1 and 1.2 ppm, on average 0.6 ppm. If a reasonable moderator change is 0.2 ppm, then changes in inlet water levels of more than 0.333% would be expected to require a moderator change of greater than 0.2 ppm and thus would require re-optimization of the moderator level. These inlet water increases of 1% were equivalent to outlet water level increases of 1.1%. Thus, if a reasonable moderator change is 0.2 ppm, then changes in outlet water levels of more than 0.367% would be expected to require a moderator change of greater than 0.2 ppm and thus would require re-optimization of the moderator level. Re-optimization may be made to the moderator level once the inlet or outlet levels change to have an increased level of more than 0.4%.

The balance inert gases usually present in the feed comprise, for example, nitrogen, argon, and/or saturated hydrocarbons such as methane or ethane. If ethane ballast is used, the chloride moderator required will be significantly higher.

"GHSV", or Gas Hourly Space Velocity, is the unit volume of gas at standard temperature and pressure (0° C., 1 atm, i.e. 101.3 kPa) passing over one unit volume of packed catalyst per hour. Preferably, if the process is carried out as a gas phase process, the GHSV is in the range of from 1,500 to 10,000. The reactor inlet pressure is preferably in the range of from 1,000 to 3,500 kPa.

The reaction temperature is typically between about 210° C. and 325° C. from the start of the run to the end of the run. Preferred start and end temperatures depend upon the particular plant design and the particular catalyst employed. Typically the reaction temperature is operated at a value which is sufficient to effect an olefin oxide production of 10,000 to 250,000 kg-mole per $m^3$ catalyst bed, preferably up to the end of the catalyst's lifetime, that is when the catalyst will be exchanged and/or rejuvenated.

The present process may be started-up by using procedures known in the art, for example from U.S. Pat. No. 4,874,879, U.S. Pat. No. 5,155,242, U.S. Pat. No. 6,717,001 and US Pub. Pat. App. 2009/0281339 which are incorporated herein by reference.

The material of the support of the supported silver-containing catalysts may be selected from a wide range of conventional materials which are considered to be inert in the presence of the olefin oxidation feed, products and reaction conditions. Such conventional materials can be natural or artificial and they may include aluminum oxides, magnesia, zirconia, silica, silicon carbide, clays, pumice, zeolites and charcoal. Alpha alumina is the most preferred material for use as the main ingredient of the porous support.

The support is typically porous and has preferably a surface area, as measured by the B.E.T. method, of less than 20 $m^2/g$ and more in particular from 0.05 to 20 $m^2/g$. Preferably the B.E.T. surface area of the support is in the range of 0.1 to 10, more preferably from 0.1 to 3.0 $m^2/g$. The B.E.T. method of measuring the surface area has been described in detail by Brunauer, Emmet and Teller in J. Am. Chem. Soc. 60 (1938) 309 316.

The catalyst comprises silver as a catalytically active metal. Appreciable catalytic activity is obtained by employing a silver content of the catalyst of at least 10 g/kg, relative to the weight of the catalyst. Preferably, the catalyst comprises silver in a quantity of from 50 to 500 g/kg, more preferably from 100 to 400 g/kg, relative to the weight of the catalyst.

The catalyst preferably comprises, in addition to silver, a further element or compound thereof. Eligible further elements may be selected from the group of nitrogen, sulfur, phosphorus, boron, fluorine, Group IA metals, Group IIA metals, rhenium, molybdenum, tungsten, chromium, titanium, hafnium, zirconium, vanadium, thallium, thorium, tantalum, niobium, gallium and germanium and mixtures thereof. Preferably the Group IA metals are selected from lithium, potassium, rubidium and cesium. Most preferably the Group IA metal is lithium, potassium and/or cesium. Preferably the Group IIA metals are selected from calcium and barium. Typically, the further element is present in the catalyst in a quantity of from 0.01 to 500 mmole/kg, more typically from 0.05 to 100 mmole/kg, calculated as the element on the total catalyst. Where possible, the further element may suitably be provided as an oxyanion, for example, as a perrhenate, sulfate, nitrate, nitrite, borate or molybdate, in salt or acid form. Salts of Group IA metals or Group IIA metals are suitable.

Preferred supported highly selective silver-containing catalysts to be used in the present invention are rhenium-containing catalysts. Such catalysts are known from U.S. Pat. No. 4,766,105 and U.S. Pat. No. 4,761,394, which are incorporated herein by reference. Broadly, these catalysts contain a catalytically effective amount of silver, a promoting amount of rhenium or compound thereof, a promoting amount of at least one further metal or compound thereof and optionally a co-promoting amount of a rhenium co-promoter selected from tungsten, molybdenum, chromium, sulfur, phosphorus, boron, and compounds thereof. More specifically at least one further metal of these rhenium-containing catalysts is/are selected from the group of Group IA metals, Group IIA metals, titanium, hafnium, zirconium, vanadium, thallium, thorium, tantalum, niobium, gallium and germanium and mixtures thereof. Preferably at least one further metal is/are selected from the Group IA metals such as lithium, potassium, rubidium and cesium and/or from the Group IIA metals such as calcium and barium. Most preferably it is lithium, potassium and/or cesium.

Preferred amounts of the components of these rhenium-containing catalysts are, when calculated as the element on the total catalyst: silver from 10 to 500 g/kg, more preferably from 10 to 400 g/kg, rhenium from 0.01 to 50 mmol/kg, further metal or metals from 10 to 3000 mg/kg, and optional rhenium co-promoter from 0.1 to 10 mmol/kg.

More preferably, the rhenium content of these catalysts is at least 0.5 mmole/kg, in particular at least 1.0 mmole/kg, more in particular at least 1.5 mmole/kg, when calculated as the element on the total catalyst. More preferably, the rhenium content of these catalysts is at most 40 mmole/kg, when calculated as the element on the total catalyst. Alternatively, the rhenium content of these catalysts, expressed relative to the surface area of the support, is preferably at least 0.0005 mmole/m$^2$, in particular at least 0.001 mmole/m$^2$, more in particular at least 0.0015 mmole/m$^2$. Preferably the rhenium content of these catalysts is at most 0.1 mmole/m$^2$, more preferably at most 0.05 mmole/m$^2$, relative to the surface area of the support.

As used herein, the quantity of Group IA metal present in the catalysts is deemed to be the quantity in so far as it can be extracted from the catalysts with de-ionized water at 100° C. The extraction method involves extracting a 10-gram sample of the catalyst three times by heating it in 20 ml portions of de-ionized water for 5 minutes at 100° C. and determining in the combined extracts the relevant metals by using a known method, for example atomic absorption spectroscopy.

As used herein, the quantity of Group IIA metal present in the catalysts is deemed to the quantity in so far as it can be extracted from the catalysts with 10% w nitric acid in de-ionized water at 100° C. The extraction method involves extracting a 10-gram sample of the catalyst by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

The olefin oxide produced may be recovered or removed by using methods known in the art, for example by absorbing the olefin oxide in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether or an alkanolamine.

Figure 3:
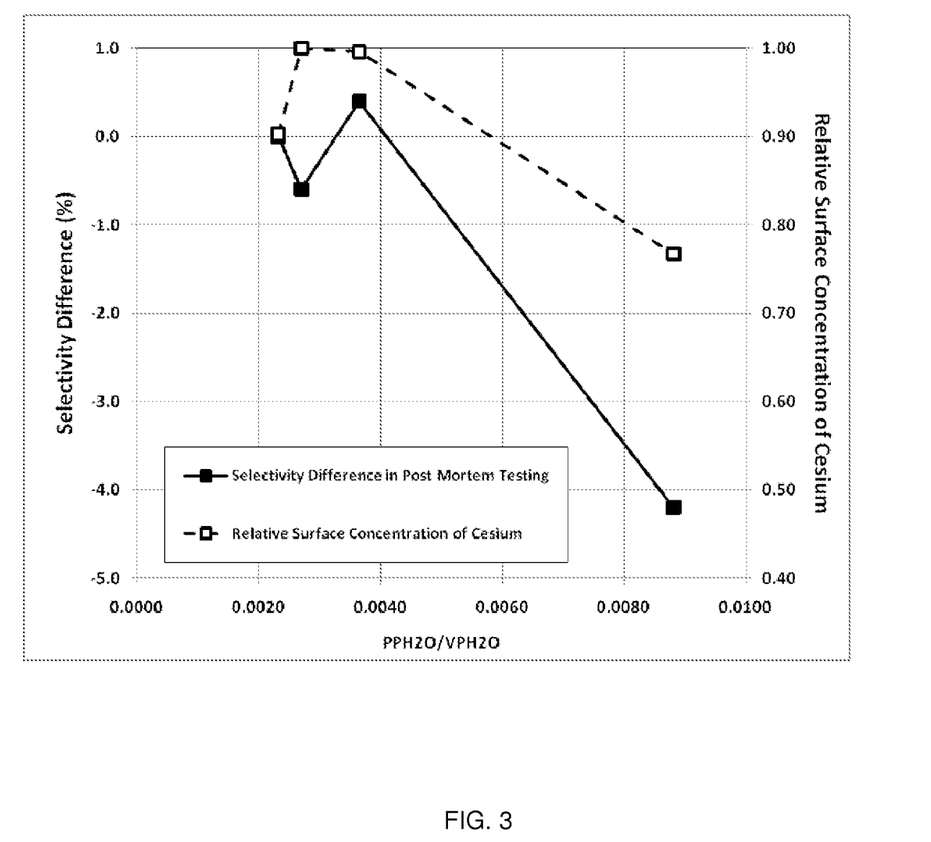
FIG. 3 depicts the relationship between selectivity and relative surface concentration of cesium at various ratios of the partial pressure of water divided by the vapor pressure of water for Plant Y.

A description of the olefin epoxidation process, including the various vessels and process steps is disclosed and discussed with regard to FIG. 3 in US Pub. Pat. App. 2009/0234144, which disclosure is incorporated herein by reference. As disclosed therein, a feed stream comprising ethylene and oxygen is charged to the tube side of shell-and-tube heat exchanger wherein it is contacted with the catalyst bed contained therein. The shell-and-tube heat exchanger is typically operated in a manner which allows an upward or downward flow of gas through the catalyst bed. The heat of reaction is removed and control of the reaction temperature, that is the temperature within the catalyst bed, is achieved by use of a heat transfer fluid, for example oil, kerosene or water, which is charged to the shell side of shell-and-tube heat exchanger and the heat transfer fluid is removed from the shell of shell-and-tube heat exchanger. The reaction product comprising ethylene oxide, unreacted ethylene, unreacted oxygen and other reaction products such as carbon dioxide and water, is withdrawn from the reactor system tubes of the shell-and-tube heat exchanger and passes to a separation system. The separation system provides for the separation of ethylene oxide from ethylene and carbon dioxide and water—typically this involves an EO recovery or removal section, a $CO_2$ absorber section and a $CO_2$ removal section.

The olefin oxide produced in the epoxidation process may be converted into a 1,2-diol, into a 1,2-diol ether, into a 1,2-carbonate or into an alkanolamine. The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten-fold molar excess of water, in a liquid phase reaction in presence of an acid catalyst, e.g. 0.5 to 1.0% w sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The conversion into the alkanolamine may comprise reacting the olefin oxide with an amine, such as ammonia, an alkyl amine or a dialkylamine. Anhydrous or aqueous ammonia may be used. Anhydrous ammonia is typically used to favour the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the organic compounds mentioned herein, for example the olefins, 1,2-diols, 1,2-diol ethers, 1,2-carbonates, alkanolamines and organic halides, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLES

Example 1

Determination of the Ratio of $PPH_2O/VPH_2O$ and Comparison to Relative Surface Concentration of Cesium and Post-Mortem Catalyst Performance The parameters needed to perform the calculations for this example are given in Table 1. Note, Steps A-E are plant operating steps and accompanying operating data. Step F is a post-mortem analysis of the catalyst.

TABLE 1

Parameters Used for Calculation of the Ratio of H2O Partial Pressure to the H2O Vapor Pressure

| | | |
|---|---|---|
| Reactor Inlet Pressure | bara | 15.0 |
| Reactor Outlet Pressure | bara | 13.3 |
| Total Tube Length | m | 12.8 |
| Reactor Inlet H2O Mole Fraction | frac. | 0.0040 |
| Inlet CO2 Mole Fraction | frac. | 0.0310 |
| Outlet CO2 Mole Fraction | frac. | 0.0437 |

Axial Temperature Profile

The EO Plant (referred to as Plant W) used in this example has multiple thermocouples in multiple tubes of the reactor allowing a direct and detailed measurement of the catalyst temperature profile. Temperatures measured at 2.1, 6.6, 10.4, 12.3 and 12.8 meters from the inlet of the reactor tube were used for comparison as catalyst samples were collected from each of these positions. The catalyst employed in this example was a high silver on alumina catalyst having a silver content of about 27% by weight, and containing promoters including cesium, lithium, tungsten and rhenium.

Axial Pressure Profile

Inlet and outlet gas pressures were measured for the reactor and the procedure outlined in Step B above was used to calculate the pressure at each of the five axial positions (2.1, 6.6, 10.4, 12.3 and 12.8 meters from the inlet of the catalyst bed).

Axial $H_2O$ Partial Pressure Profile

The inlet water mole fraction was available from direct measurements made by the Karl Fischer titration method and were confirmed by process calculations of the inlet water mole fraction. See, e.g., ASTM E203-08.

Direct measurements of the outlet water mole fraction were not available, so the reaction stoichiometry and measured $CO_2$ concentrations were used to determine the mole fraction of water in the reactor outlet as explained in Step C above.

The axial $H_2O$ partial pressure profile was calculated as described in Step C, using the axial temperature and pressure profiles and inlet and outlet $H_2O$ mole fractions.

Axial $H_2O$ Vapor Pressure Profile

The axial $H_2O$ vapor pressure profile was calculated as described in Step D above using the measured axial temperature profile and the referenced vapor pressure correlation.

Calculation of the Ratio of $H_2O$ Partial Pressure to $H_2O$ Vapor Pressure

The result of the Axial $H_2O$ Partial Pressure Profile was divided by the results of Axial $H_2O$ Vapor Pressure Profile to give the axial profile of the ratio of $H_2O$ partial pressure to the $H_2O$ vapor pressure in the catalyst bed.

Analysis of Catalyst Samples

X-ray photoelectron spectroscopy was conducted on the samples from 2.1, 6.6, 10.4, 12.3 and 12.8 meters from the inlet of the reactor tube and the relative surface concentration of cesium was determined as described below. Microreactor performance testing was conducted on each sample and the selectivity difference as described below was determined for each sample.

Characterization of Spent Catalyst Samples

Calculation of Relative Surface Concentration of Cesium

The following steps provide a full description of the methodology required to determine the surface concentration of cesium (or any other promoter) remaining on the catalyst after operation in a reactor.

i. Once a reactor is shutdown, the catalyst must be removed in sections and samples clearly labelled so that the precise axial position (or distance from the inlet) that the sample occupied in the catalyst bed is known.

ii. Samples from multiple sections are then crushed and homogenized prior to taking small sub-samples.

iii. The sub-samples are then analyzed by X-ray Photoelectron Spectroscopy (XPS) to determine the average concentration of cesium on the surface of the crushed catalyst.

iv. X-ray photoelectron spectroscopy analyses were preformed on a VG ESCALAB mkII X-ray photoelectron spectrometer. Non-monochromatized Al kα (1484.6 eV) X-rays were used as the excitation source. The electron kinetic energy analyzer was a 150 degree spherical sector analyzer equipped with a three channeltron detection system. All spectra were obtained in the constant analyzer pass energy mode and the pass energy was set at 50 eV. Prior to analysis, samples were lightly crushed with a mortar and pestle and mounted onto a sample stub using double-sided tape. The analysis area was roughly 3 mm×5 mm. The Al2s peak was used for charge correction and was corrected to 118.9 eV. Linear baselines were used for measuring the peak heights. Peak intensities were converted to relative molar values using empirically derived sensitivity factors (SF) and the following relationship:

$$\text{Relative number of atoms} = \frac{(Cs3d5 \text{ Intensity}/(Cs3d5 \text{ SF}) \text{ times } 100}{(Al2s \text{ intensity}/(Al2s \text{ SF}))}$$

The relative number of Cs atoms measured for each sample were normalized to the inlet value.

Performance Testing of Spent Catalyst Samples

1. Samples taken from each axial position in the reactor were crushed and 1-5 g were loaded into microreactors.

2. Each sample was tested in a microreactor under average conditions similar to that which the catalyst experienced during operation in the commercial reactor.

3. The selectivity for conversion of ethylene to ethylene oxide was determined at these operating conditions.

Figure 1:
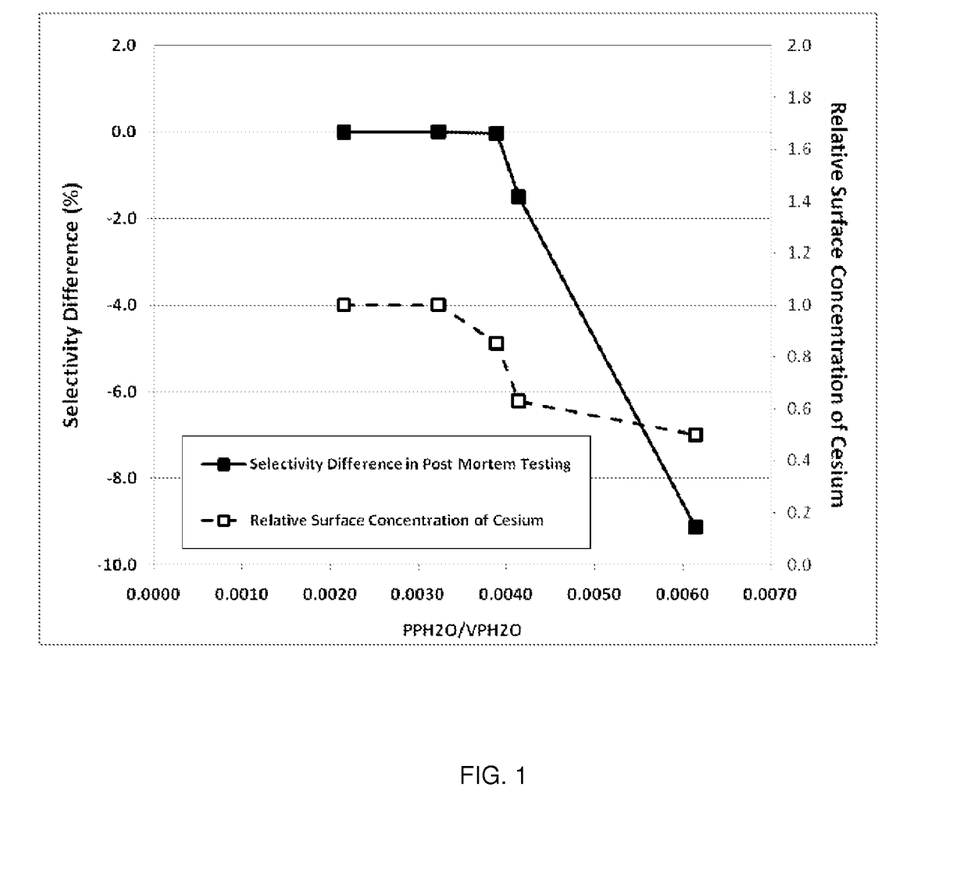
FIG. 1 depicts the relationship between selectivity and relative surface concentration of cesium at various ratios of the partial pressure of water divided by the vapor pressure of water for Plant W.

Results for Example 1 are shown in Table 2 and FIG. 1.

TABLE 2

Measured and calculated axial profile values for Plant W.

| | | | | | | |
|---|---|---|---|---|---|---|
| Distance from Inlet of Reactor Tubes | m | 2.1 | 6.6 | 10.4 | 12.3 | 12.8 |
| Gas Temperature in Catalyst Bed | ° C. | 252 | 259 | 264 | 266 | 244 |
| Gas Pressure in Catalyst Bed | bara | 14.7 | 14.1 | 13.6 | 13.3 | 13.3 |
| H2O Partial Pressure | bara | 0.089 | 0.148 | 0.193 | 0.215 | 0.220 |
| H2O Vapor Pressure | bara | 41.19 | 45.90 | 49.67 | 51.87 | 35.73 |
| Ratio | | 0.0022 | 0.0032 | 0.0039 | 0.0041 | 0.0061 |
| Relative Surface Concentration of Cesium | | 1.00 | 1.00 | 0.85 | 0.63 | 0.50 |
| Selectivity Difference in Post Mortem Testing | | 0.0 | 0.0 | 0.0 | −1.5 | −9.1 |

As shown in Table 2, the temperature at 12.8 meters from the inlet of the reactor tube is only 244° C., which is the result of the injection of cold kerosene near the outlet of the reactor. The results shown in Table 2 dramatically reveal that when the ratio of $PPH_2O/VPH_2O$ is less than 0.0040, there is uniform ageing of the catalyst and no selectivity deficit due to operation under excessive concentrations of water vapor. Where the ratio of $PPH_2O/VPH_2O$ is greater than 0.0040 there is a negative selectivity difference indicating a loss in selectivity.

Example 2

Changing Moderator Levels as Water Levels Change

Example 2 shows the impact on optimum moderator levels with various catalysts as the inlet water level changes:

A commercially available, Re-containing catalyst with 13.2 wt % silver was operated in a laboratory reactor under the following conditions: inlet (dry) composition of 7.3% $O_2$, 30.9% $C_2H_4$, and 1.6% $CO_2$, with 18.3 barg inlet pressure, and 3900 gas hourly space velocity, controlling the temperature to maintain a ΔEO of 2.50%. When the inlet water level was increased from 0% to 0.93% and re-optimized, the optimal moderator level decreased 22%. When the inlet water level was increased from 0% to 2.01% and re-optimized, the optimal moderator level decreased 26%. The corresponding outlet water levels for the three cases were 0.64%, 1.73%, and 3.07%.

A commercially available, Re-containing catalyst with 17.5 wt % silver was operated in a laboratory reactor under the following conditions: inlet (dry) composition of 7.3% $O_2$, 30.9% $C_2H_4$, and 1.6% $CO_2$, with 17.8 barg inlet pressure, and 4000 gas hourly space velocity, controlling the temperature to maintain a ΔEO of 2.49%. When the inlet water level was increased from 0% to 0.95% and re-optimized, the optimal moderator level decreased 20%. When the inlet water level was increased from 0% to 2.04% and re-optimized, the optimal moderator level decreased 28%. The corresponding outlet water levels for the three cases were 0.58%, 1.62%, and 3.10%.

A commercially available, Re-containing catalyst with 27.5 wt % silver was operated in a laboratory reactor under the following conditions: inlet (dry) composition of 7.3% $O_2$, 30.9% $C_2H_4$, and 1.6% $CO_2$, with 17.8 barg inlet pressure, and 3460 gas hourly space velocity, controlling the temperature to maintain a ΔEO of 2.48%. When the inlet water level was increased from 0% to 0.96% and re-optimized, the optimal moderator level decreased 21%. When the inlet water level was increased from 0% to 2.05% and re-optimized, the optimal moderator level decreased 27%. The corresponding outlet water levels for the three cases were 0.62%, 1.77%, and 2.88%.

A commercially available, Re- and $SO_4$-containing catalyst with 17.5 wt % silver was operated in a laboratory reactor under the following conditions: inlet (dry) composition of 7.3% $O_2$, 30.9% $C_2H_4$, and 1.6% $CO_2$, with 18.3 barg inlet pressure, and 4000 gas hourly space velocity, controlling the temperature to maintain a ΔEO of 2.48%. When the inlet water level was increased from 0% to 0.96% and re-optimized, the optimal moderator level decreased 30%. When the inlet water level was increased from 0% to 2.05% and re-optimized, the optimal moderator level decreased 28%. The corresponding outlet water levels for the three cases were 0.57%, 1.68%, and 3.16%.

A commercially available, Re-containing catalyst with 29.0 wt % silver was operated in a laboratory reactor under the following conditions: inlet (dry) composition of 7.5% $O_2$, 25.4% $C_2H_4$, and 3.9% $CO_2$, with 19.0 barg inlet pressure, and 4900 gas hourly space velocity, controlling the temperature to maintain a ΔEO of 1.91%. When the inlet water level was increased from 0% to 0.90% and re-optimized, the optimal moderator level decreased 11%. When the inlet water level was increased from 0% to 2.01% and re-optimized, the optimal moderator level decreased 10%. The corresponding outlet water levels for the three cases were 0.50%, 1.49%, and 2.76%.

Example 3

Determination of the Ratio of $PPH_2O/VPH_2O$ and Comparison to Relative Surface Concentration of Cesium and Post-Mortem Catalyst Performance The parameters needed to perform the calculations for this example are given in Table 3. Note, Steps A-E are plant operating steps and accompanying operating data. Step F is a post-mortem analysis of the catalyst.

TABLE 3

Parameters Used for Calculation of the Ratio of H2O Partial Pressure to the H2O Vapor Pressure for Plant X

| | | |
|---|---|---|
| Reactor Inlet Pressure | bara | 22.5 |
| Reactor Outlet Pressure | bara | 21.1 |
| Total Tube Length | m | 12.0 |
| Reactor Inlet H2O Mole Fraction | frac. | 0.0034 |
| Inlet CO2 Mole Fraction | frac. | 0.0034 |
| Outlet CO2 Mole Fraction | frac. | 0.0135 |

Axial Temperature Profile

The EO Plant (referred to as Plant X) used in this example uses water-cooled reactors and has an outlet gas temperature measurement that is representative of the catalyst temperature from the 1.5 m position in the catalyst bed to the outlet of the catalyst bed. Thus, the catalyst temperature for each position at 1.5, 2.7, 5, 10.2, and 10.8 meters were assumed to be equal to the outlet gas temperature measured for the reactor. The catalyst employed in this example was a silver on alumina catalyst having a silver content of about 13% by weight, and containing promoters including cesium, lithium, tungsten and rhenium.

Axial Pressure Profile

Inlet and outlet gas pressures were measured for the reactor and the procedure outlined in Step B above was used to calculate the pressure at each of the five axial positions (1.5, 2.7, 5, 10.2, and 10.8 meters from the inlet of the catalyst bed).

Axial $H_2O$ Partial Pressure Profile

The inlet water mole fraction was available from direct measurements made by the Karl Fischer titration method and were confirmed by process calculations of the inlet water mole fraction. See, e.g., ASTM E203-08.

Direct measurements of the outlet water mole fraction were not available, so the reaction stoichiometry and measured $CO_2$ concentrations were used to determine the mole fraction of water in the reactor outlet as explained in Step C above.

The axial $H_2O$ partial pressure profile was calculated as described in Step C, using the axial pressure profile and inlet and outlet $H_2O$ mole fractions.

Axial $H_2O$ Vapor Pressure Profile

The axial $H_2O$ vapor pressure profile was calculated as described in Step D above using the measured axial temperature profile and the referenced vapor pressure correlation.

Calculation of the Ratio of $H_2O$ Partial Pressure to $H_2O$ Vapor Pressure

The result of the Axial $H_2O$ Partial Pressure Profile was divided by the results of Axial $H_2O$ Vapor Pressure Profile to give the axial profile of the ratio of $H_2O$ partial pressure to the $H_2O$ vapor pressure in the catalyst bed.

Analysis of Catalyst Samples

X-ray photoelectron spectroscopy was conducted on the samples from 1.5, 2.7, 5, 10.2, and 10.8 meters from the inlet of the reactor tube and the relative surface concentration of cesium was determined as described below. Microreactor performance testing was conducted on each sample and the selectivity difference as described below was determined for each sample.

Characterization of Spent Catalyst Samples

A similar analysis as done in Example 1 was performed on the spent catalyst samples of Example 3. Results for Example 3 are shown in Table 4 and FIG. 2.

TABLE 4

| Measured and calculated axial profile values for Plant X | | | | | | |
|---|---|---|---|---|---|---|
| Distance from Inlet of Reactor Tubes | m | 1.5 | 2.7 | 5.0 | 10.2 | 10.8 |
| Gas Temperature in Catalyst Bed | ° C. | 242.6 | 242.6 | 242.6 | 242.6 | 242.6 |
| Gas Pressure in Catalyst Bed | bara | 22.3 | 22.2 | 21.9 | 21.3 | 21.3 |
| H2O Partial Pressure | bara | 0.104 | 0.126 | 0.166 | 0.255 | 0.265 |
| H2O Vapor Pressure | bara | 34.95 | 34.95 | 34.95 | 34.95 | 34.95 |
| Ratio | | 0.0030 | 0.0036 | 0.0048 | 0.0073 | 0.0076 |
| Relative Surface Concentration of Cesium | | 1.00 | 0.94 | 0.82 | 0.82 | 0.79 |
| Selectivity Difference in Post Mortem Testing | | 0.0 | 0.0 | −0.9 | −0.8 | −1.8 |

Figure 2:
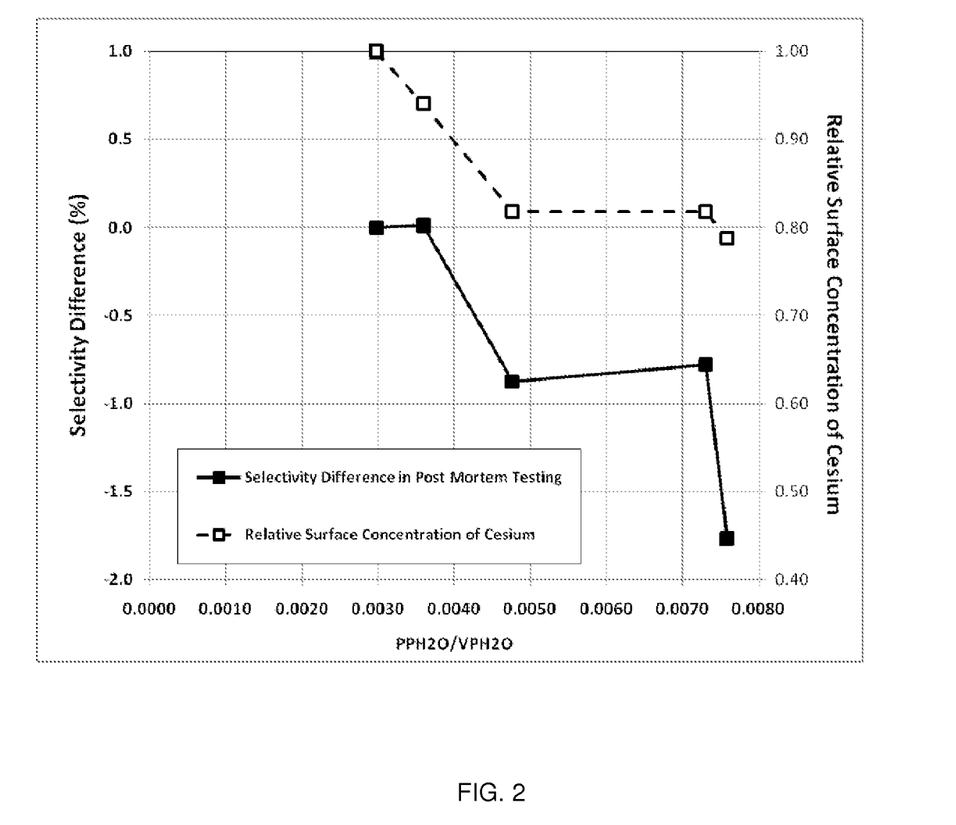
FIG. 2 depicts the relationship between selectivity and relative surface concentration of cesium at various ratios of the partial pressure of water divided by the vapor pressure of water for Plant X.

FIG. 2 depicts the relationship between selectivity and relative surface concentration of cesium at various ratios of the partial pressure of water divided by the vapor pressure of water for Plant X.

The results shown in Table 4 reveal that when the ratio of $PPH_2O/VPH2O$ is less than 0.0040, there is uniform and reduced ageing of the catalyst relative to positions where the ratio of $PPH_2O/VPH_2O$ is >0.0040. Where the ratio of $PPH_2O/VPH_2O$ is greater than 0.0040 there is a negative selectivity difference indicating a loss in selectivity.

Example 4

Determination of the Ratio of $PPH_2O/VPH_2O$ and Comparison to Relative Surface Concentration of Cesium and Post-Mortem Catalyst Performance The parameters needed to perform the calculations for this example are given in Table 5. Note, Steps A-E are plant operating steps and accompanying operating data. Step F is a post-mortem analysis of the catalyst.

TABLE 5

| Parameters Used for Calculation of the Ratio of H2O Partial Pressure to the H2O Vapor Pressure for Plant X | | |
|---|---|---|
| Reactor Inlet Pressure | bara | 16.8 |
| Reactor Outlet Pressure | bara | 15.2 |
| Total Tube Length | m | 12.0 |
| Reactor Inlet H2O Mole Fraction | frac. | 0.0033 |
| Inlet CO2 Mole Fraction | frac. | 0.0548 |
| Outlet CO2 Mole Fraction | frac. | 0.0719 |

Axial Temperature Profile

The EO Plant (referred to as Plant Y) used in this example uses kerosene-cooled reactors and has outlet gas temperature measurements, coolant temperature measurements, and a peak temperature difference between catalyst and coolant temperature is available. This plant also returns sub-cooled kerosene to the bottom of the reactor to reduce the gas temperature in the reactor outlet. To approximate the axial profile of the gas temperature in the catalyst bed in this case, it was assumed that the gas temperature at 1 meter from the inlet of the reactor tube was equal to the coolant temperature of 267° C., measured in the plant. Then the peak temperature difference (PTD) of 16.5° C. was assumed to occur at a position of 11.3 meters from the inlet of the reactor tube. The following linear interpolation was used to estimate the gas temperature at various positions between the 1 meter and 11.3 meter points in the catalyst bed.

Gas Temperature (z) =

Coolant Temperature (° C.) + Peak Temperature Difference (° C.) times (z − 1(meter))/(11.3(meter) − 1(meter))

e.g.,

Gas Temperature (3.4 m) =

267.3 + 16.5 times (3.4 − 1)/(11.3 − 1) = 271° C.

Where, Gas Temperature (z) is the gas temperature at the axial position z in the catalyst bed and is used for positions from 1 to 11.3 meters from the inlet of the reactor tube. The value of z is the distance from the inlet of the reactor tube. This equation is not applicable for any portion of the catalyst bed from 0-1 meter as this is a heatup zone from a much lower inlet gas temperature. The equation is not applicable for the portion of the catalyst bed from 11.3 m to the exit of the tube at 12.8 meters due to the effects of the sub-cooled coolant injection near the reactor outlet. In this example samples were collected from positions 3.4, 4.6, 8.2, and 12.5 meters from the inlet of the reactor tube. Thus, the equation was used to estimate the temperature for the first three positions. For the position at 12.5 meters it was assumed that the gas temperature was equal to the outlet gas temperature due to the cooling effects of the sub-cooled coolant.

The catalyst employed in this example was a silver on alumina catalyst having a silver content of about 13% by weight, and containing promoters including cesium, lithium, tungsten and rhenium.

Axial Pressure Profile

Inlet and outlet gas pressures were measured for the reactor and the procedure outlined in Step 2 above was used to calculate the pressure at each of the five axial positions (3.4, 4.6, 8.2, and 12.5 meters from the inlet of the catalyst bed).

Axial $H_2O$ Partial Pressure Profile

The inlet water mole fraction was available from direct measurements made by the Karl Fischer titration method and were confirmed by process calculations of the inlet water mole fraction. See, e.g., ASTM E203-08.

Direct measurements of the outlet water mole fraction were not available, so the reaction stoichiometry and measured $CO_2$ concentrations were used to determine the mole fraction of water in the reactor outlet as explained in Step C above.

The axial $H_2O$ partial pressure profile was calculated as described in Step C, using the axial pressure profile and inlet and outlet $H_2O$ mole fractions.

Axial $H_2O$ Vapor Pressure Profile

The axial $H_2O$ vapor pressure profile was calculated as described in Step D above using the measured axial temperature profile and the referenced vapor pressure correlation.

Calculation of the Ratio of $H_2O$ Partial Pressure to $H_2O$ Vapor Pressure

The result of the Axial $H_2O$ Partial Pressure Profile was divided by the results of Axial $H_2O$ Vapor Pressure Profile to give the axial profile of the ratio of $H_2O$ partial pressure to the $H_2O$ vapor pressure in the catalyst bed.

Analysis of Catalyst Samples

X-ray photoelectron spectroscopy was conducted on the samples from 3.4, 4.6, 8.2, and 12.5 meters from the inlet of the reactor tube and the relative surface concentration of cesium was determined as described below. Microreactor performance testing was conducted on each sample and the selectivity difference as described below was determined for each sample.

Characterization of Spent Catalyst Samples

Calculation of Relative Surface Concentration of Cesium

A similar analysis as done in Example 1 was performed on the spent catalyst samples of Example 4. Results for Example 4 are shown in Table 6 and FIG. 3.

TABLE 6

Measured and calculated axial profile values for Plant Y.

| | | | | | |
|---|---|---|---|---|---|
| Distance from Inlet of Reactor Tubes | m | 3.4 | 4.6 | 8.2 | 12.5 |
| Gas Temperature in Catalyst Bed | ° C. | 271.1 | 273.1 | 278.9 | 243.3 |
| Gas Pressure in Catalyst Bed | bara | 16.5 | 16.4 | 15.9 | 15.4 |
| H2O Partial Pressure | bara | 0.130 | 0.156 | 0.230 | 0.312 |
| H2O Vapor Pressure | bara | 55.93 | 57.66 | 63.09 | 35.39 |
| Ratio | | 0.0023 | 0.0027 | 0.0037 | 0.0088 |
| Relative Surface Concentration of Cesium | | 0.90 | 1.00 | 1.00 | 0.77 |
| Selectivity Difference in Post Mortem Testing | | 0.0 | −0.6 | 0.4 | −4.2 |

The results shown in Table 6 reveal that when the ratio of $PPH_2O/VPH_2O$ is less than 0.0040, there is uniform and reduced ageing of the catalyst relative to positions where the ratio of $PPH_2O/VPH_2O$ is >0.0040. Where the ratio of $PPH_2O/VPH_2O$ is greater than 0.0040 there is a negative selectivity difference indicating a loss in selectivity.

FIG. 3 depicts the relationship between selectivity and relative surface concentration of cesium at various ratios of the partial pressure of water divided by the vapor pressure of water for Plant Y.

What is claimed is:

1. A process for the production of an olefin oxide, which process comprises reacting a feed comprising an olefin and oxygen in the presence of a catalyst bed comprising silver-containing catalyst loaded in a reactor tube, wherein the presence of water at any point in the catalyst bed is controlled such that the ratio of the partial pressure of water ($PPH_2O$) divided by the vapor pressure of water ($VPH_2O$) is less than 0.006.

2. The process as claimed in claim 1, wherein the ratio of the partial pressure of water ($PPH_2O$) divided by the vapor pressure of water ($VPH_2O$) is less than 0.004 over at least 50 percent of the catalyst bed length.

3. The process as claimed in claim 1, wherein the ratio of the partial pressure of water ($PPH_2O$) divided by the vapor pressure of water ($VPH_2O$) is less than 0.004 over at least 80 percent of the catalyst bed length.

4. The process as claimed in claim 1, wherein the olefin is ethylene, and the process includes an ethylene oxide reactor containing multiple ethylene oxide reactor tubes, an ethylene oxide removal section, a $CO_2$ absorber section, and a $CO_2$ removal section.

5. The process as claimed in claim 4, wherein the catalyst contains a cesium promoter.

6. The process as claimed in claim 5, wherein the catalyst also contains a rhenium promoter.

7. The process as claimed in claim 6, wherein the presence of water in the ethylene oxide reactor is controlled by utilizing one or more of the following process steps:
   a) increased cooling of an overhead stream coming from an ethylene oxide removal section and/or a $CO_2$ removal section that return to the ethylene oxide reactor;
   b) diversion of less of a recycle gas through a $CO_2$ absorber section;
   c) operation of an ethylene oxide absorber and a $CO_2$ absorber at lower temperature;
   d) increasing the Gas Hourly Space Velocity at fixed ethylene oxide production to reduce the water concentration gradient increase in the ethylene oxide reactor;
   e) reduction in ethylene oxide production per unit volume of catalyst to reduce the amount of water formed in the ethylene oxide reactor; and
   f) operation of the ethylene oxide reactor at higher temperature than required to increase the vapor pressure of water in the ethylene oxide reactor tubes.

8. The process as claimed in claim 7, wherein the ethylene oxide reactor is operated at a temperature of about 210° C. to about 325° C.

9. The process as claimed in claim 7, wherein the amount of $CO_2$ present in the ethylene oxide reactor is controlled at a level of less than 3.0 mole percent.

10. The process as claimed in claim 7, wherein cooling is increased to the overhead stream coming from the ethylene oxide removal section and/or $CO_2$ removal section that return to the ethylene oxide reactor.

11. The process as claimed in claim 7, wherein the level of recycle gas through the $CO_2$ absorber is decreased.

12. The process as claimed in claim 7, wherein the ethylene oxide absorber and $CO_2$ absorber are operated at lower temperatures.

13. The process as claimed in claim 7, wherein the Gas Hourly Space Velocity at fixed ethylene oxide production is increased in order to reduce the water concentration gradient increase in the ethylene oxide reactor.

14. The process of claim 7, wherein the ethylene oxide production per unit volume of catalyst is reduced to reduce the amount of water formed in the ethylene oxide reactor.

15. The process of claim 7, wherein the ethylene oxide reactor is operated at a higher temperature than required in order to increase the vapor pressure of water in the ethylene oxide reactor tubes.

16. The process as claimed in claim 5 wherein the catalyst comprises, in addition to silver and cesium, a co-promoter selected from lithium, potassium and compounds thereof.

17. The process as claimed in claim 6, wherein the catalyst comprises, in addition to silver, cesium, rhenium or compound thereof, a rhenium co-promoter selected from one or more of lithium, tungsten, molybdenum, chromium, sulfur, phosphorus, boron, and compounds thereof.

18. The process of claim 1, wherein the ratio of the partial pressure of water ($PPH_2O$) divided by the vapor pressure of water ($VPH_2O$) is less than 0.004 over the entire length of the catalyst bed.

19. The process of claim 1 including a moderator selected from the group consisting of $C_1$ to $C_8$ organic halides.

20. The process of claim 19 wherein the level of moderator is adjusted higher as the water level is lowered during the process for the production of an olefin oxide.

21. The process of claim 19 wherein the level of moderator is re-optimized if the inlet water level changes by more than 0.4% during the process for the production of an olefin oxide.

22. The process of claim 19 wherein the level of moderator is re-optimized if the outlet water level changes by more than 0.4% during the process for the production of an olefin oxide.

23. A method of making a 1,2-diol, a 1,2-diol ether or an alkanolamine comprising converting an olefin oxide into the 1,2-diol, the 1,2-diol ether, 1,2-carbonate or the alkanolamine by reacting the olefin oxide with water, an alcohol, carbon dioxide or an amine, wherein the olefin oxide has been obtained by a process as claimed in claim 1.

24. The method of claim 23 wherein the olefin oxide is ethylene oxide, and the ethylene oxide is reacted with water to form ethylene glycol.

\* \* \* \* \*